United States Patent [19]

Chiulli

[11] 4,112,932
[45] Sep. 12, 1978

[54] LAPAROSCOPIC CANNULA
[76] Inventor: Robert D. Chiulli, 71 Cherry St., Somerville, Mass. 02143
[21] Appl. No.: 771,519
[22] Filed: Feb. 24, 1977
[51] Int. Cl.$^2$ .......................... A61B 1/00; A61B 17/36
[52] U.S. Cl. .................................... 128/3; 128/303.11
[58] Field of Search .............................. 128/3–8, 128/303.11, 344, 347, 348, 341, 274, 349 BU

[56] References Cited
U.S. PATENT DOCUMENTS 3,747,812  7/1973  Karman et al. ................ 128/274
3,957,082  5/1976  Fuson et al. ................... 128/274

Primary Examiner—Robert W. Michell
Assistant Examiner—Henry S. Layton
Attorney, Agent, or Firm—Scott R. Foster

[57] ABSTRACT

A cannula for surgical use comprising a base member having a bore therethrough, a tubular member bounding the bore and extending outwardly from a first side of the base member, and a turret member connected to a second side of the base member and having first and second aperture therein, the turret member being movable relative to the base member to selectively place a selected aperture in or out of alignment with the bore to open or close a passageway through the instrument.

9 Claims, 3 Drawing Figures

LAPAROSCOPIC CANNULA

BACKGROUND OF THE INVENTION

1. Field of the Invention

This invention relates to surgical instruments and is directed more particularly to an cannula.

2. Description of the Prior Art

Laparoscopy, a method for direct visualization of intra-abdominal contents is used as a means for evaluating abdominal pathology. Use of the laparoscope, in conjunction with a method of introducing instruments into the abdomen, permits these instruments to be manipulated under direct visualization and has thereby made possible the performance of various surgical procedures without a laparotomy.

Obstetrical procedures are particularly amenable to this method of investigation, especially exploratoy evaluation, tubal ligation by cautery or the Fallop ring, and cautery of endometriotic sites. All of the instruments required for such procedures can be passed through a narrow cannula and the procedure achieved as efficiently as with open manipulation.

The laparoscopic cannula procedure is as follows. A tubular needle connected to a low pressure carbon dioxide gas source is inserted through the umbilicus into the peritoneal cavity of the abdomen. This area is essentially the abdominal sac containing the viscera which must be evaluated or operated on. Carbon dioxide is instilled through the needle producing distension of the abdomen and expanding the anatomical space between the viscera and the abdominal wall. The needle is then withdrawn and puncture at the needle site is effected with trocar and cannula. The trocar is now removed and the laparoscope substituted by passing it through the cannula. Direct visualization of the abdominal contents is obtained.

In order to permit manipulation and/or operation within the abdomen, an additional puncture by a trocar and cannula at a second site is made. The trocar is withdrawn and introduction of various instruments such as probes, grasping forceps, cautery devices, or fallopian tube ring applicators may be accomplished through the second cannula while watching the procedure through the laparoscope disposed in the primary cannula.

Upon completion of the procedure, the secondary cannula is withdrawn, followed by the primary cannula and each puncture site is closed by a single stitch.

Cannulas in use today generally comprise a base member having a bore extending therethrough, and an elongated tubular metal member, or cannula tube, in alignment with the bore and extending outwardly from the base member. The base member is provided with a short tubular member, or seal mount, in alignment with the bore and extending in the opposite direction of the cannula tube. The free end of the seal mount is provided with a sealing member, usually of rubber or other elastomeric material, having a hole at its center. The cannula is ordinarily used initially in conjunction with a trocar — an elongated sharp pointed metal device having a diameter which closely approximates the inside diameter of the cannula and having a hilt at one end. The trocar is pushed through the hole in the sealing member, passes through the base member, coming to rest with the trocar hilt adjacent the sealing member and the point of the trocar extending beyond the free end of the elongated cannula tube. In so doing, the elastomeric seal is maximally distended and frequently torn by the trocar's point.

In use, the trocar and cannula are, as a unit, driven through an abdominal wall distended by gas pressure, as described above. Once the cannula is in place the trocar has served its purpose and is replaced by an instrument, or number of instruments in series, most of which have a diameter smaller than that of the trocar so as to permit mobility within the cannula. Since the sharpened trocar has both enlarged and probably cut the elastomeric seal upon initial insertion, the seal achieved with instruments of smaller diameter is often inadequate, resulting in a persistent leak and consequent deflation of the abdomen. Therefore, it often becomes necessary to change the sealing member due to seal damage or an appreciable discrepancy in instrument diameter as compared to that of the precedent trocar.

During the change of the sealing member and/or instruments, the surgeon or his assistant must manually block the orifice of the exposed end of the cannula so as to minimize the loss of intra-abdominal gas. Such manual exertions are suboptimal inasmuch as the transition is awkward, usually permitting a goodly portion of the gas to escape through the cannula.

Another problem arises when an electrical cauterizing instrument is used in conjunction with the cannula. The instrument may contact the conductive metal tubular member and cause inadvertent singeing of the tissue surrounding the member.

SUMMARY OF THE INVENTION

An object of the present invention is, therefore, the provision of a cannula which permits removal of the trocar and other instruments therefrom without significant escape of gas.

A further object is to provide such a device in which various instruments may be introduced without the necessity of changing sealing members with each change of instruments.

A still further object is to provide such a device of non-electrically conductive material to prevent accidental cautery of the perimeter of the opening through which the device enters a body.

With the above and other objects in view, as will hereinafter appear, a feature of the present invention is the provision of a cannula including a base member having a bore therethrough, a tubular member aligned with the bore and extending outwardly therefrom, a turret member connected to the base member, and having first and second aperture therein, the turret member being movable relative to the base member to place a selected aperture in or out of alignment with the bore means.

In accordance with a further feature of the invention, the apertures with seal mount members extending therefrom, each seal mount member being provided with a sealing means disposed at the free end thereof, each sealing means being adapted to accommodate an instrument to be used in conjunction therewith.

In accordance with a still further feature of the invention, the device is of non-electrically conductive material.

The above and other features of the invention, including various novel details of construction and combinations of parts, will now be more particularly described with reference to the accompanying drawings and pointed out in the claims. It will be understood that the particular device embodying the invention is shown by way of illustration only and not as a limitation of the invention. The principles and features of this invention may be employed in various and numerous embodiments without departing from the scope of the invention.

BRIEF DESCRIPTION OF THE DRAWINGS

Reference is made to the accompanying drawings in which is shown an illustrative embodiment of the invention from which its novel features and advantages will be apparent.

DESCRIPTION OF THE PREFERRED EMBODIMENTS

Figure 1:
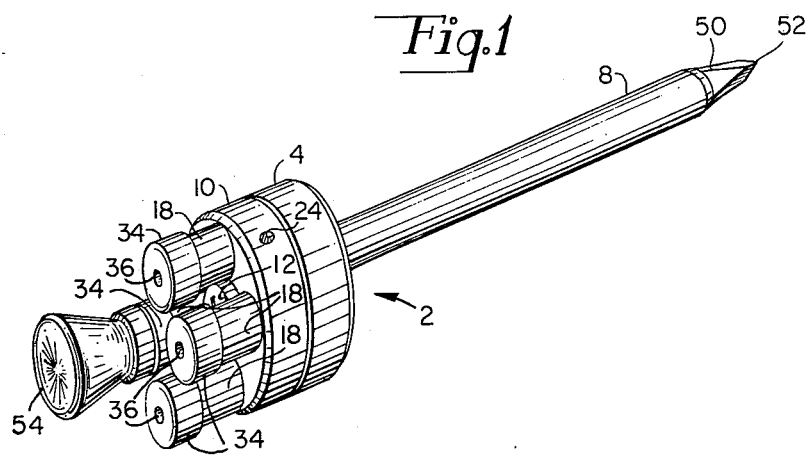
FIG. 1 is a perspective view of an illustrative embodiment of the invention, shown in combination with a trocar.
Figure 2:
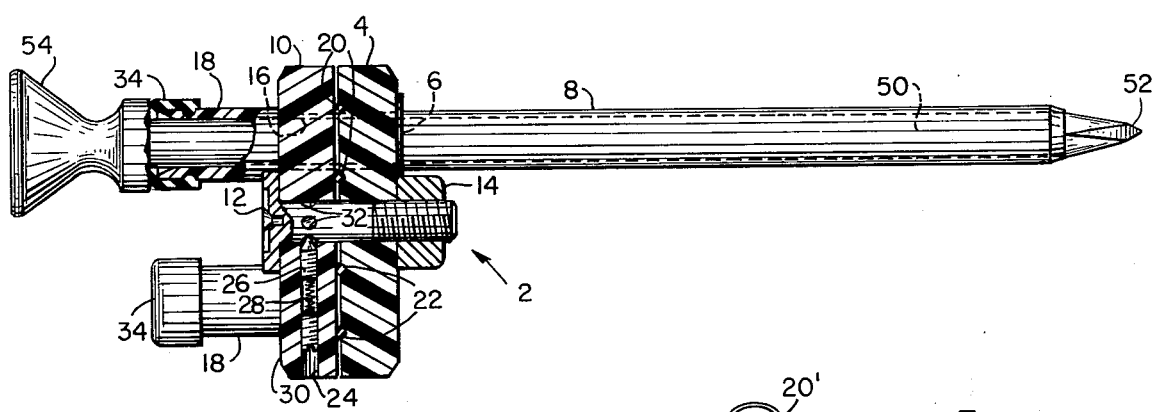
FIG. 2 is a side elevational view, partly in section, of the assembly shown in FIG. 1.

Referring to FIGS. 1 and 2, it will be seen that there is provided a cannula 2 including a base member 4 having a bore 6 therethrough. A tubular member or cannula tube 8, is attached to the base member 4 and is disposed in alignment with the bore 6. For ease of assembly, the cannula tube 8 may be anchored in the bore 6.

A turret member 10 is connected to the base member 4 by way of a bolt 12 and nut 14. The turret member 10 is rotatable about the bolt and nut 12, 14 and relative to the base member 4. The turret member 10 is provided with aperture means 16 (one aperture 16 being shown in FIG. 2), and seal mount members 18 aligned therewith. Again, for ease of assembly the seal mount members 8 may be disposed in part within the apertures 16 and secured therein. The turret member 10 may be rotated so as to bring a selected member 18, and thereby a selected aperture 16 into or out of alignment with the bore 6.

A sealing ring 20 is disposed about the bore 6 and adjacent the turret member 10, to prevent escape of gas through the bore 6 and between the base member 4 and turret member 10. A second ring 22 may be used to balance the assembly. The turret member 10 may be provided with a bore 24 which receives a plunger 26, a coil spring 28, and a screw member 30, the plunger 26 being spring biased into engagement with the bolt 12 which is provided with a series of detents 32 adapted to receive an end of the plunger 26. Thus, positions of aperture-bore alignment and non-alignment may be indicated by discernible "clicks" as the turret member is rotated.

Each seal mount member 18 is provided with a sealing member 34 disposed on the free end thereof. The sealing members 34 comprise essentially caps of rubber or elastomeric material and have a central hole 36 therein for receiving and sealing a trocar or other instrument.

Figure 3:
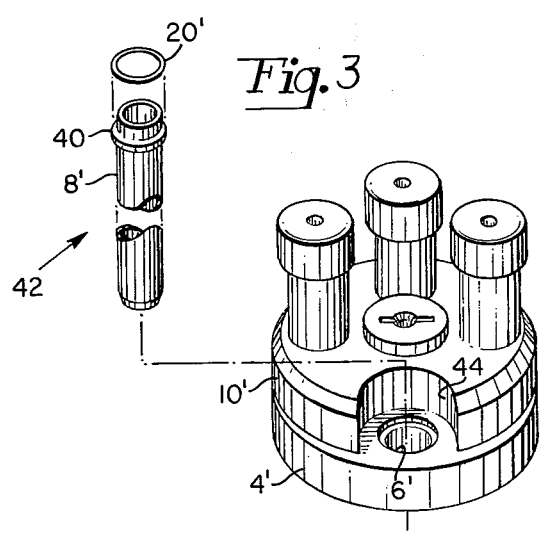
FIG. 3 is an exploded perspective view of an alternative embodiment.

Referring to FIG. 3, it will be seen that the tubular member 8' may be provided with a circular flange member 40 and sealing ring 20', this assembly constituting a replaceable and disposable cannula tube assembly 42 insertable in the bore 6' of the base member 4' through a cut-away portion 44 of the turret member 10'. The flange member 40 rests upon an internal shoulder in the bore 6', the upper end of the tubular member 8', as shown in FIG. 3, interfacing with the turret member 10'. In this embodiment, after the cannula tube assembly 42 is in place, the turret member is rotated to capture the cannula tube assembly, the cannula tube 8' being sealed until it is aligned with one of the turret member apertures 16.

In either embodiment, it is desirable that the cannula tube member 8, 8' be of a non-electrically conducting material.

In operation, the cannula 2 is first used in conjunction with a trocar 50 comprising an elongated pointed nail-like member having a point 52 at one end thereof and a hilt 54 at the other end thereof. Anticipating the instruments to be used subsequent to the trocar, appropriate sealing members 34 are placed on the members 18, the sealing members being provided with various sizes of holes 36 to accommodate different sizes or types of instruments. An abdomen extended by gas is punctured by the point 52 of the trocar 50 and the cannula tube 8 entered through the opening so made. The trocar is then withdrawn until it is clear of the base member 4 and still disposed in the turret member 10 and seal mount member 18. At this point, the sealing ring 20 and sealing member 34 prevent loss of gas through the instrument.

The turret member 10 is then rotated until the next discernible "click" is caused by the plunger 26 snapping into a detent 32. At this point there is no aperture 16 in alignment with the bore 6 which is sealed by the turret 10 and the sealing ring 20. The trocar may then be withdrawn without escape of gas through the instrument. The next desired instrument may then be placed in another seal mount and rotated into alignment with the bore 6. In like manner, any number of instruments may be used. If a seal is used in a manner so as to make it unsuitable for the next instrument to be introduced therethrough, the seal may be changed at any time when its respective mount 18 is not in alignment with the bore 6 and there will be no escape of gas through the cannula.

It is to be understood that the present invention is by no means limited to the particular constructions herein disclosed and/or shown in the drawings, but also comprises any modifications or equivalents within the scope of the disclosure.

Having thus described my invention, what I claim as new and desire to secure by Letters Patent of the United States is:

1. A cannula comprising a base member having a bore therethrough, a tubular member aligned with said bore and extending outwardly from a first side of said base member, a turret member connected to a second side of said base member, said turret member having first and second apertures therein alignable individually with said bore, said turret member being movable relative to said base member to place a selected one of said apertures in alignment with said bore, said turret member being further movable to place said selected aperture out of alignment with said bore.

2. The invention according to claim 1 in which said turret member is provided with seal mount members bounding said first and second apertures and extending outwardly from said turret member.

3. The invention according to claim 2 in which each said seal mount member is provided with a sealing means disposed at the free end thereof.

4. The invention according to claim 1 including sealing means disposed about said bore and engaging said turret member for sealing off said bore when said bore is not in alignment with said aperture means and for sealing said bore whereby to maintain integrity within the aligned passages when said bore is in alignment with said selected aperture.

5. The invention according to claim 1 in which said base member, said turret member, and said tubular member are of electrically non-conductive material.

6. The invention according to claim 1 in which said turret member is slidingly movable relative to said base member.

7. The invention according to claim 6 in which said turret member is pivotally movable relative to said base member.

8. The invention according to claim 1 in which said tubular member is provided with a flange and sealing ring proximate one end thereof, said tubular member, flange and sealing ring constituting a cannula tube assembly, said assembly being held in place by location of said flange between said base member and said turret member, said turret member being provided with a recess which may be aligned with said bore to permit removal of said cannula tube assembly and replacement thereof through said recess.

9. The invention according to claim 8 in which said cannula tube assembly is of non-electrically conductive material.

* * * * *